United States Patent
Cho et al.

(10) Patent No.: US 9,381,171 B2
(45) Date of Patent: Jul. 5, 2016

(54) COMPOSITION INCLUDING DAPSONE FOR PREVENTING OR TREATING SIDE EFFECT OF STEROID IN SUBJECT AND USE OF THE COMPOSITION

(71) Applicant: Samsung Electronics Co., Ltd., Suwon-si, Gyeonggi-do (KR)

(72) Inventors: Sungchun Cho, Hwaseong-si (KR); Sangchul Park, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/577,690

(22) Filed: Dec. 19, 2014

(65) Prior Publication Data

US 2015/0174085 A1 Jun. 25, 2015

(30) Foreign Application Priority Data

Dec. 19, 2013 (KR) .......................... 10-2013-0159643
Oct. 30, 2014 (KR) .......................... 10-2014-0149333

(51) Int. Cl.
*A61K 31/145* (2006.01)
*A61K 31/573* (2006.01)

(52) U.S. Cl.
CPC ............. *A61K 31/145* (2013.01); *A61K 31/573* (2013.01)

(58) Field of Classification Search
CPC .................................................... A61K 31/145
See application file for complete search history.

(56) References Cited

U.S. PATENT DOCUMENTS 7,799,782 B2 * 9/2010 Munson et al. ............ 514/234.5
2007/0203216 A1   8/2007 Ebert et al.

FOREIGN PATENT DOCUMENTS

| JP | 2006-522744 | 10/2006 |
| KR | 2008-0034925 A | 4/2008 |
| KR | 2009-0097922 A | 9/2009 |
| WO | WO 02/098403 A1 | 12/2002 |
| WO | WO 2013/085351 A1 | 6/2013 |

OTHER PUBLICATIONS

Konohana et al., Clin. Exp. Dermatol., 1994, 19(4): 367.*
Kamada et al., Drug Ther., 1994, 23(11): 55-58 or 61-62.*
Hoes et al. "Current view of glucocorticoid co-therapy with DMARDs in rheumatoid arthritis", *Nature Reviews*, 6: 693-702 (2010).
Metselaar et al., "Complete Remission of Experimental Arthritis by Joint Targeting of Glucocorticoids With Long-Circulating Liposomes", *Arthritis & Rheumatism*, 48(7): 2059-2066 (2003).
Paul-Clark et al., "Potent antiarthritic properties of a glucocorticoid derivative, NCX-1015, in an experimental model of arthritis", *PNAS*, 99(3): 1677-1682 (2002).
Perretti et al., "Generation of innovative anti-inflammatory and anti-arthritic glucocorticoid derivatives that release NO: the nitro-steroids", *Digestive and Liver Disease*, 35, Suppl 2: S41-S48 (2003).
Hoffman et al., "Balancing muscle hypertrophy and atrophy", *Nature Medicine*, 10(6): 584-585 (2004).

* cited by examiner

*Primary Examiner* — Rei-Tsang Shiao
(74) *Attorney, Agent, or Firm* — Leydig, Voit & Mayer, Ltd.

(57) ABSTRACT

A composition including dapsone for preventing or treating a side effect of a steroid in a subject, and methods for preventing or treating a side effect of a steroid using the composition.

9 Claims, 8 Drawing Sheets
(1 of 8 Drawing Sheet(s) Filed in Color)

_US 9,381,171 B2_

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic primer for mouse atrogin-1/MAFbx

<400> SEQUENCE: 1
cacattctct cctggaaggg c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer for mouse atrogin-1/MAFbx

<400> SEQUENCE: 2
ttgataaagt cttgagggga a                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer for mouse MuRF-1

<400> SEQUENCE: 3
acgagaagaa gagcgagctg                                                20

<210> SEQ ID NO 4
<211> LENGTH: 22
<212> TYPE: DNA
<213> ORGANISM: Artificial Sequence
<220> FEATURE:
<223> OTHER INFORMATION: Synthetic primer for mouse MuRF-1

<400> SEQUENCE: 4
cttggcactt gagagaggaa gg                                             22
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic primer for mouse GAPDH

<400> SEQUENCE: 5
catggccttc cgtgttccta                                           20

<210> SEQ ID NO 6
<211> LENGTH: 17
<212> TYPE: DNA
<213> ORGANISM: Artificial Sequence
<220> FEATURE:
<223> OTHER INFORMATION: Synthetic primer for mouse GAPDH

<400> SEQUENCE: 6
gcggcacgtc agatcca                                              17
```

COMPOSITION INCLUDING DAPSONE FOR PREVENTING OR TREATING SIDE EFFECT OF STEROID IN SUBJECT AND USE OF THE COMPOSITION

RELATED APPLICATIONS

This application claims the benefit of Korean Patent Application No. 10-2013-0159643, filed on Dec. 19, 2013, and Korean Patent Application No. 10-2014-0149333, filed on Oct. 30, 2014, in the Korean Intellectual Property Office, the disclosures of which are incorporated herein in their entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,589 Bytes ASCII (Text) file named "719271_ST25.TXT," created on Dec. 18, 2014.

BACKGROUND

1. Field

The present disclosure relates to a composition including dapsone for preventing or treating a side effect of a steroid in a subject and use of the composition.

2. Description of the Related Art

Dapsone is also known as diaminodiphenylsulfone (DDS), and its IUPAC name is 4-[(4-aminobenzene)sulfonyl]aniline. Dapsone is an antibacterial substance that is most commonly used in combination with rifampicin and clofazimine as multidrug therapy (MDT) for the treatment of _Mycobacterium leprae_ infections (e.g., leprosy). It is also a second-line treatment for prophylaxis against _Pneumocystis_ pneumonia (PCP) caused by _Pneumocystis jirovecii_ in HIV patients of which cluster of differentiation 4 (CD4) counts are less than 200 per milligram. Dapsone is used in combination with pyrimethamine in the treatment of malaria. Dapsone is commercially available in both topical and oral formulations.

Currently available methods to treat a side effect caused by steroid therapy are exemplified by the following: administration of insulin or oral anti-diabetic drugs in the case of diabetes; administration of antacids or H2 blocking agents in the case of digestive tract symptoms; administration of vitamin D or calcium in the case of osteoporosis; administration of an ocular tension lowering agent in the case of glaucoma; and administration of psychotropic drugs in the case of mental aberration or depression.

In spite of these known methods of treatment, there is still a need to develop methods that prevent or treat a side effect of steroid therapy.

SUMMARY

Provided is a composition for preventing or treating a side effect of a steroid in a subject, the composition including dapsone, a pharmaceutically acceptable salt, a solvate, a polymorph, or a combination thereof.

Provided is a composition for increasing activity of Akt, decreasing activity of FOXO1, decreasing activity of Atrogin-1, decreasing activity of MuRF-1, decreasing phosphorylation of a glucocorticoid receptor, decreasing nuclear translocation of the phosphorylated glucocorticoid receptor, or a combination thereof, the composition including dapsone, a pharmaceutically acceptable salt, a solvate, a polymorph, or a combination thereof.

Provided is a method of preventing or treating a side effect of a steroid in a subject, the method including administering dapsone, a pharmaceutically acceptable salt, a solvate, a polymorph, or a combination thereof to a subject in need thereof.

Provided is a method of preventing or treating a side effect of a steroid in a subject through an increase in activity of Akt, a decrease in activity of FOXO1, a decrease in activity of Atrogin-1, a decrease in activity of MuRF-1, a decrease in phosphorylation of a glucocorticoid receptor, a decrease in nuclear translocation of the phosphorylated glucocorticoid receptor, or a combination thereof, the method including administering dapsone, a pharmaceutically acceptable salt, a solvate, a polymorph, or a combination thereof to a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the exemplary embodiments, taken in conjunction with the accompanying drawings in which.

DETAILED DESCRIPTION

Figure 1:
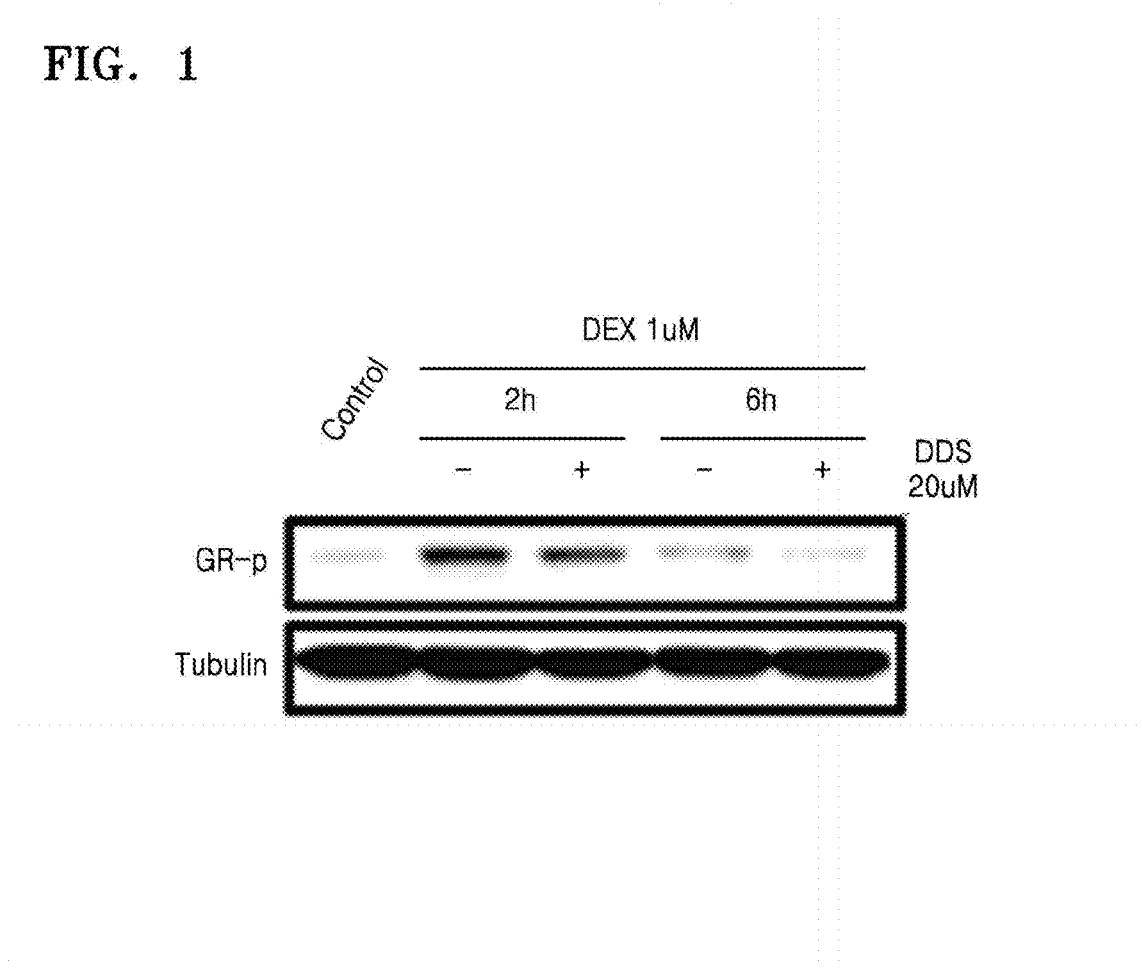
FIG. 1 is a western blot analysis of phosphorylated glucocorticoid receptor (GR-p) of C2C12 myoblasts cultured in the presence of dexamethasone and/or dapsone.

Reference will now be made in detail to exemplary embodiments, examples of which are illustrated in the accompanying drawings, wherein like reference numerals refer to like elements throughout. The present exemplary embodiments may have different forms and should not be construed as being limited to the descriptions set forth herein. Accordingly, the exemplary embodiments are described below by referring to the figures merely to explain aspects of the embodiments. As used herein, the term "and/or" includes any and all combinations of one or more of the associated listed items.

Provided is a composition for preventing or treating a side effect of a steroid in a subject, the composition including dapsone, a pharmaceutically acceptable salt, a solvate, a polymorph, or a combination thereof.

Dapsone is called diaminodiphenylsulfone (DDS), and its IUPAC name is 4-[(4-aminobenzene)sulfonyl]aniline. Dapsone may have a structure of Chemical Formula I below.

(Chemical Formula I)

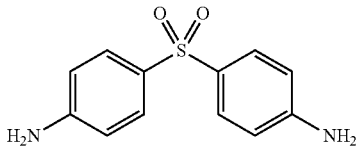

Dapsone may be commercially available, or may be directly synthesized or extracted from natural substances. In order to further improve water solubility of dapsone, it may be mixed with water and treated in an autoclave. A treatment with high pressure sterilization in the autoclave may be performed in a manner that is commonly used in the art. For example, high pressure sterilization may be performed in the autoclave for 15 to 20 minutes at a temperature of 121° C. and a pressure of 151 psi. When dapsone is mixed with water, and then, treated with high pressure sterilization, dapsone may obtain solubility at which dapsone may be dissolved at a desired concentration, regardless of water-insoluble properties of untreated dapsone. In addition, when administered to, e.g., a mouse, dapsone may be present in a suitable range of effective blood levels. Due to the treatment with high pressure sterilization, dapsone may retain its activity, i.e., antibiotic effects against bacteria.

As used herein, the term 'pharmaceutically acceptable salt' refers to any salt that does not cause a significantly adverse stimulation on an organism to which a compound is administered and that does not adversely affect the biological activity and physical properties of a compound. The pharmaceutically acceptable salt may include, for example, an inorganic salt, an organic salt, or a metal salt. Examples of the inorganic salt include hydrochloride, bromate, phosphate, sulphate, and disulfate. Examples of the organic salt include formate, acetate, propionate, lactate, oxalate, tartrate, malate, maleate, citrate, fumarate, besylate salt, camsylate salt, edisylate salt, salt of trichloroacetic acid, salt of trifluoroacetic acid, benzoate, gluconate, methanesulfonate, glycolate, succinate, 4-toluenesulfonate, salt of galacturonate, embonate, glutamate, methane sulfonate, ethane sulfonate, benzene sulfonate, p-toluenesulfonate, and aspartate. Examples of the metal salt include calcium salt, sodium salt, magnesium salt, strontium salt, and potassium salt.

The pharmaceutically acceptable salt, the solvate, the polymorph, or a combination thereof is an active ingredient for the prevention or treatment of a side effect of a steroid in a subject, and may be administered to a subject in an effective amount. The effective amount of the active ingredient may be appropriately selected according to cells or subjects selected by one of ordinary skill in the art. The effective amount of the active ingredient per the composition may be in a range of about 1 μg to about 1,000 mg, e.g., about 0.1 mg to about 1,000 mg, about 0.1 mg to about 500 mg, about 0.1 mg to about 100 mg, about 0.1 mg to about 50 mg, about 0.1 mg to about 25 mg, about 1 mg to about 1,000 mg, about 1 mg to about 500 mg, about 1 mg to about 100 mg, about 1 mg to about 50 mg, about 1 mg to about 25 mg, about 5 mg to about 1,000 mg, about 5 mg to about 500 mg, about 5 mg to about 100 mg, about 5 mg to about 50 mg, about 5 mg to about 25 mg, about 10 mg to about 1,000 mg, about 10 mg to about 500 mg, about 10 mg to about 100 mg, about 10 mg to about 50 mg, or about 10 mg to about 25 mg.

The side effect of a steroid may be caused by a treatment using steroids, or by an increase in the amount of steroid used for treatment, in a subject. The treatment using steroids may refer to administration of a steroid drug to a subject so as to prevent or treat a disease or a symptom of a disease in a subject.

The side effect of the treatment using steroids may include declines in immunity; adrenal cortical insufficiency; impaired glucose tolerance such as induced-diabetes, aggravated diabetes or elevated blood glucose level; ulcers in digestive tract, bleeding in digestive tract, gastrointestinal perforation, and hemorrhagic pancreatitis; convulsion and intracranial hypertension; mental aberration and depression; osteoporosis, e.g., bone hypometabolism including spinal compression fractures; aseptic necrosis in head bone, e.g., femur or humerus fractures; myopathy, e.g., muscle weakness associated with amyotrophia, such as declines in proximal muscle weight or proximal muscle weakness, muscle dysfunction, and weight less; glaucoma, ocular hypertension, and posterior subcapsular cataract; thrombus, e.g., thromboelastography; cardiac rupture by myocardial infarction; aggravated attack of asthma; anaphylaxis by injection; moon face and buffalo hump; sodium-water retention, e.g., edema, weight gain, and hypocalcemic alkalosis; developmental disturbance of children; menstrual disorder; decrease in the number of sperm and in the movement of sperm; acne, hirsutism, alopecia, and pigmentation; thinning skin, skin vulnerability, hypodermic congestion, linear purpura, facial erythema, fats, and cellulitis; hindrance of wound healing; hypersensitiveness (e.g., rash), itching, and hiccup; euphoria, insomnia, headache, and dizziness; dyshidrosis, polyuria, and leukocytosis; fatty liver and nitrogen nonequilibrium; synergistic GOT, GPT, and ALP; hyperlipidemia, hypercholesterolemia, and steroid nephrosis; vomiting, stomachache, chest pain, abdominal distension, hydrodipsomania, diarrhea, and hyperphagia; exophthalmos and retinopathy by central serous chorioretinopathy; myalgia, arthralgia, fever, and fatigability; atrophy, dent, and weight loss of local tissues caused by intramuscular, intracutaneous, and subcutaneous injection; aggravated thrombus, phlebitis, pain, swelling, and tenderness caused by intravenous injection; withdrawal syndrome; fever, headache, inverse fatigue, general malaise, enervation, and shock as systemic symptoms; anorexia, low appetite, nausea and vomiting, and diarrhea in digestive system; and headache, anxiety symptoms, and excitation in nervous system; convulsion, disturbance of consciousness, myalgia, arthralgia, etc. The side effect of a steroid may include at least one selected from the group consisting of amyotrophia, insufficient (e.g., reduced) muscle strength, myalgia, arthralgia, impaired glucose tolerance, low appetite, weight loss, bone hypometabolism, declines in immunity, and fatigability.

Myopathy may include diseases or conditions associated with symptoms such as gradual loss muscle mass caused by a side effect of steroid use. The myopathy may cause weak physical condition, and accordingly, cause aggravated health condition or incompetent body performance.

Dapsone may be used for the prevention or treatment of sarcopenia caused by steroid use. As used herein, the term "sarcopenia" refers to gradual loss of skeletal muscle mass typically associated with aging, but which also occurs as a side effect of steroid treatment. The types of the skeletal muscle includes, without limitation, a soleus (SOL) muscle, an extensor digitorum longus (EDL) muscle, a gastrocnemius (GA) muscle, a tibialis anterior (TA) muscle, or a combination thereof.

The steroid therapy that causes the side effect to be reduced by dapsone treatment can be steroid therapy for any disease. A target disease for steroid therapy may include a disease caused by a hyperactive immune system. Other examples of a target disease for steroid therapy include endocrine disorders, e.g., chronic adrenal cortical insufficiency (e.g., primary, secondary, hypophyseal, or iatrogenic chronic adrenal cortical insufficiency), acute adrenal cortical insufficiency (e.g., adrenal crisis), adrenogenital syndrome, subacute thyroiditis, thyrotoxicosis (e.g., thyroid(toxic) crisis), malignant exopthalmosis associated with a thyroid disease, and isolated ACTH deficiency; rheumatic diseases, e.g., chronic articular rheumatism, juvenile articular rheumatism (Still's disease), rheumatism fever (e.g., rheumatic carditis), and polymyalgia rheumatica; collagen diseases, e.g., lupus erythematosus (e.g., systemic and chronic discoid lupus erythematosus), systemic vasculitis (e.g., aortitis syndrome, periarteritis nodosa, polyarteritis, and Wegener's granulomatosis), and polymyositis (e.g., dermatomyositis); renal diseases, e.g., nephrosis and nephrosis syndrome; heart diseases, e.g., congestive heart failure; allergic diseases, e.g., bronchial asthma, asthmatic bronchitis (e.g., asthmatic bronchitis of children), allergy addition by chemical substances other than drugs (e.g., drug rash, toxic exanthema), and serum sickness; severe infectious diseases, e.g., severe infectious diseases (in combination with chemotherapy; hematodyscrasia, e.g., hemmolytic anemia (suspected with immunity), leukemia (e.g., acute leukemia, transformation in chronic myelocytic leukemia, chronic lymphocytic) (including leukemia cutis), granulopenia (e.g., essential or secondary granulopenia), purpura (thrombocytopenic and athrombocytopenic purpura), anemia aplastic, and hemorrhagic diathesis by disturbances of coagulation factors; digestive tract diseases, e.g., localized enteritis and ulcerative colitis; severe consumption diseases, e.g., improvement of general condition (including terminal cancer or sprue) associated with severe consumption diseases; liver diseases, e.g., fulminant hepatitis (which is considered clinically severe), acute cholestatic hepatitis, chronic hepatitis (e.g., active hepatitis, recurrent acute hepatitis, and cholestatic hepatitis) (refer that hepatitis having continuous significant abnormality in liver function without reaction to general treatment is defined as refractory hepatitis), and hepatic cirrhosis (e.g., active hepatitis, hepatitis associated with refractory ascites, and hepatitis associated with cholestasia); lung diseases, e.g., sarcoidosis (except bilateral hilar lymphadenopathy) and diffuse interstitial pneumonia (e.g., pulmonary fibrosis) (including radiation pneumonitis); tuberculous diseases (in combination with antituberculosis drug), pulmonary tuberculosis (limited to miliary tuberculosis and severe tuberculosis), tuberculous meningitis, tuberculous pleurisy, tuberculous peritonitis, and tuberculous pericarditis; neurological disorders, e.g., encephalomyelitis (including encephalitis and encephalomyelitis) (increased intracranial pressure is observed in the case of primary encephalitis, and a drug is prepared for short-time use when the effect is insufficient with other agents), peripheral neuritis (including Guillain-Barre syndrome), myotonia, myasthenia gravis, multiple sclerosis (including neuromye litis optica), chorea minor, and facial nerve paralysis; malignant tumors, e.g., malignant lymphoma (lymphosarcomatosis, reticulum cell sarcoma, Hodgkin's disease, reticulosis cutis, and mushroom-like polyposis) and similar diseases (muscular spasm disease), eosinophilic granuloma, and metastasis of breast cancer recurrence; other medical diseases, e.g., idiopathic glycopenia and ill cryptogenic fever; and infectious diseases, e.g., SARS. Also included would be, for instance, steroid therapy applied for the purposes other than treating disease, such as for inhibiting rejection responses that are caused by organ transplantation, such as liver or renal transplantation.

The steroid drug used in the steroid therapy may include a glucocorticoid. As used herein, the term "glucocorticoid" refers to a class of steroid hormones that bind to a glucocorticoid receptor, which is present in almost all vertebrate animal cells. The glucocorticoid receptor is also known as a nuclear receptor subfamily 3, group C, member 1 (NR3C1), which is a receptor to which cortisol and other glucocorticoids bind. The glucocorticoid receptor may have an amino acid sequence of NP_000167 (human) and NP_032199 (mouse). The glucocorticoid receptor may be encoded by a nucleotide sequence of NM_000176 (human) and NM_008173 (mouse).

The steroid drug may include, for example, at least one selected from the group consisting of cortisol, hydrocortin, cortisone, prednisolone, methyl prednisolone, triamcinolone, triamcinolone acetonide, paramethasone, dexamethasone, betamethasone, hexoestrol, methimazole, fluocinonide, fluocinolone acetonide, fluorometholone, beclometasone dipropionate, estriol, diflorasone diacetate, diflucortolone valerate, and difluprednate.

The side effect of a steroid may be caused by inhibited (decreased) activity of Akt, increased activity of FOXO1, increased activity of Atrogin-1, increased activity of MuRF-1, or a combination thereof, in a cell, tissue, or subject (patient), for example, a muscle cell, kidney cell, or a combination thereof. As used herein, the term "increasing activity" or "increased activity" can be any increase in activity as compared to a suitable control, e.g., a cell, tissue, or subject (patient) as appropriate that has not been subject to steroid therapy and, thus, exhibits "normal" FOXO1, Atrogin-1, and MuRF-1 activity. Similarly, the terms "inhibited activity," "inhibited activity," "decreasing activity," or "decreased activity" can be any decrease in activity as compared to a suitable control, e.g., a cell, tissue, or subject (patient) as appropriate that has not been subject to steroid therapy and, thus, exhibits "normal" FOXO1, Atrogin-1, and MuRF-1 activity. The increase or decrease in activity may be caused by an increase or decrease in biosynthesis of the protein itself (e.g., increase or decrease in gene expression) or an increase or decrease in specific activity of protein itself as compared to a control. In this regard, dapsone used in the manner described herein concurrently or subsequently to steroid treatment may cause an increase in activity of Akt, a decrease in activity of FOXO1, a decrease in activity of Atrogin-1, a decrease in activity of MuRF-1, or a combination thereof, in a cell, tissue, or subject (patient) as compared to a cell, tissue, or subject (patient) of the same type treated with the steroid alone, without dapsone. In addition, dapsone used in the manner described herein concurrently or subsequently to steroid treatment may decrease phosphorylation of a glucocorticoid receptor compared to a control subject and/or decrease nuclear translocation of the phosphorylated glucocorticoid receptor compared to a cell, tissue, or subject (patient) of the same type treated with the steroid alone, without dapsone.

The dapsone may be used (e.g., administered) before, simultaneously, or after administering the steroid drug. In the case of simultaneous administration, dapsone may be administered with the steroid drug as part of the same composition or the dapsone and steroid can be in two separate compositions.

Dapsone can be administered as a pharmaceutical composition or functional food composition (e.g., an enhanced or fortified food). The pharmaceutical composition may include a pharmaceutically acceptable diluent or a carrier. The carrier may include an excipient, a disintegrant, a binder, a lubricant, or a combination thereof. The excipient may include microcrystalline cellulose, lactose, low-substituted hydroxypropyl cellulose, or a combination thereof. The disintegrant may include sodium starch glycolate, anhydrous dibasic calcium phosphate, or a combination thereof. The binder may include polyvinyl pyrrolidone, low-substituted hydroxypropyl cellulose, hydroxypropyl cellulose, or a combination thereof. The lubricant may include magnesium stearate, silicon dioxide, talc, or a combination thereof.

The composition may be formed in a formulation for oral or parenteral administration. The formulation for oral administration may include granules, powders, liquids, tablets, capsules, dry syrup, or a combination thereof. The formulation for parenteral administration may include an injectable drug or a dermatological preparation. The dermatological preparation may include cream, gel, ointment, skin emulsion, skin suspension, transdermal patch, drug-containing bandage, lotion, or a combination thereof.

As used herein, the term 'prevention' encompasses the inhibition of a side effect of a steroid or delay the onset of the side effect of a steroid (e.g., glucocorticoid) upon administration of the composition.

As used herein, the term 'treatment' encompasses any reduction in a side effect of a steroid, or improving or beneficially changing a side effect of a steroid.

According to another embodiment, there is provided a composition for increasing activity of Akt, decreasing activity of FOXO1, decreasing activity of Atrogin-1, decreasing activity of MuRF-1, decreasing phosphorylation of a glucocorticoid receptor, decreasing nuclear translocation of the phosphorylated glucocorticoid receptor, or a combination thereof, in a cell, tissue, or subject (patient). The subject may a subject that has been treated with a steroid. The composition includes dapsone, a pharmaceutically acceptable salt, a solvate, a polymorph, or a combination thereof Akt refers to protein kinase B (PKB) which is a serine/threonine-specific protein kinase that plays a key role in multiple cellular processes such as glucose metabolism, apoptosis, cell proliferation, transcription, and cell migration. In this regard, the activity of Akt1 may be the activity of the serine/threonine-specific protein kinase. Akt1 is a key signaling protein in the cellular pathways related to skeletal hypertrophy. Akt may include Akt1, Akt2, Akt3, or a combination thereof, wherein Akt1 may have an amino acid sequence of P31749. In addition, Akt1 may have an amino acid sequence encoded by a nucleotide sequence of NM_005163.

Forkhead box protein O1 (FOXO1) also known as forkhead in rhabdomyosarcoma is a protein that in humans is encoded by the FOXO1 gene. FOXO1 may be a transcription factor that plays an important role in the regulation of gluconeogenesis and glycogenolysis by insulin signaling. The activity of FOXO1 may include the activity of a transcription factor that is capable of affecting the expression of MuRF-1, which is specific to muscles, and that plays a key role in muscle weakness associated with muscular atrophy. FOXO1 may have an amino acid sequence of NP_002006 (human) and NP_062713 (mouse). FOXO1 may be encoded by a nucleotide sequence of NM_002015 (human) and NM_019739 (mouse).

Atrogin-1 also known as F-box only protein 32 (FBXO32) is a protein that in humans is encoded by the FBXO32 gene. The FBXO32 gene encodes a member of the F-box protein family, which is characterized by an approximately 40 amino acid motif, the F-box. The F-box proteins constitute one of the four subunits of the ubiquitin protein ligase complex called SKP1-cullin-F-box (SCF), which functions in phosphorylation-dependent ubiquitination. In this regard, the activity of Atrogin-1 may be the level of the capability of constituting the ubiquitin protein ligase complex or the activity of the ubiquitin protein ligase of the complex.

Muscle RING-finger protein-1 (MuRF-1) also known as E3 ubiquitin-protein ligase TRIM36 is an enzyme that in humans is encoded by the TRIM63 gene. In this regard, the activity of MuRF-1 may include the activity of the E3 ubiquitin-protein ligase. MuRF-1 may have an amino acid sequence of NP_115977 (human) and NP_001039048 (mouse). In addition, MuRF-1 may be encoded by a nucleotide sequence of NM_032588 (human) and NM_001039048 (mouse).

According to another embodiment, there is provided a method of preventing or treating a side effect of a steroid in a subject, the method including administering dapsone, a pharmaceutically acceptable salt, a solvate, a polymorph, or a combination thereof to a subject.

The administration may be carried out in a manner widely known in the art. For example, the administration may be directly performed on a subject through intravenous, intramuscular, oral, transdermal, mucosal, intranasal, intratracheal, or subcutaneous ways. The administration may be carried out systemically or locally, and for example, may be carried out topically on a site where fibrosis is present.

The terms "dapsone, a pharmaceutically acceptable salt, a solvate, a polymorph, or a combination thereof" and "side effect of a steroid" may be the same as defined in connection with the other embodiments described above. The "dapsone, a pharmaceutically acceptable salt, a solvate, a polymorph, or a combination thereof" may be in the form of the composition described above.

The subject may have a side effect of steroid. The subject may have a side effect of a steroid caused by a treatment using a steroid or an increase in the amounts of a steroid in the subject as described above.

The side effect of a steroid may be any as described herein, such as at least one selected from the group consisting of amyotrophy, hypofunction in muscular strength, myalgia, arthralgia, impaired glucose tolerance, low appetite, weight loss, bone hypometabolism, low immunity, and fatigability.

The side effect of a steroid may be caused by inhibited (decreased) activity of Akt, increased activity of FOXO1, increased activity of Atrogin-1, increased activity of MuRF-1, or a combination thereof, in a cell, tissue, or subject (patient), for example, muscle cell, kidney cell, or a combination thereof. The subject may be a mammal having a decreased activity of Akt, increased activity of FOXO1, increased activity of Atrogin-1, increased activity of MuRF-1, or a combination thereof compared to a cell, tissue, or subject (patient) as appropriate that has not been subject to steroid therapy and, thus, exhibits "normal" FOXO1, Atrogin-1, and MuRF-1 activity. Increased or decreased activity can be determined by comparison of activity levels from a test sample (sample from a patient) to a suitable control, e.g., a control level of activity of Akt, a control level of activity of FOXO1, a control level of activity of Atrogin-1, a control level of activity of MuRF-1, or a combination thereof. The control level may a predetermined level. The predetermined level may be determined by considering the level of activity of FOXO1, the level of activity of Atrogin-1, the level of activity of MuRF-1, or a combination thereof measured or obtained from a subject not having a side effect of a steroid and/or a subject not receiving a steroid treatment and, thus, exhibiting "normal" activity levels of these proteins. Alternatively, the control level can be considering the level of activity of FOXO1, the level of activity of Atrogin-1, the level of activity of MuRF-1, or a combination thereof measured or obtained from a subject undergoing steroid therapy (e.g., glucocorticoid therapy) and having a side effect of the steroid therapy, thus, exhibiting known inhibited (decreased) activity of Akt, increased activity of FOXO1, increased activity of Atrogin-1, increased activity of MuRF-1, or a combination thereof. For example, the predetermined level may be determined by considering the average level of activity of FOXO1, the level of activity of Atrogin-1, the level of activity of MuRF-1, or a combination thereof measured or obtained from a plurality of subjects not receiving a steroid treatment and, thus, exhibiting normal activity levels, or a plurality of subjects undergoing steroid therapy (e.g., glucocorticoid therapy) and having a side effect of the steroid therapy, thus, exhibiting known inhibited (decreased) activity of Akt, increased activity of FOXO1, increased activity of Atrogin-1, increased activity of MuRF-1, or a combination thereof.

The determination that a subject has inhibited (decreased) activity of Akt, increased activity of FOXO1, increased activity of Atrogin-1, increased activity of MuRF-1, or a combination thereof can be determined according to a predetermined proximity of the measured levels to a control. For example, with regard to decreased activity of Akt, the predetermined level may be 60%, 70%, 80%, 90%, 95%, 97%, 99%, or 99.5% of the activity of Akt in subjects not having a side effect of a steroid and/or subjects not receiving a steroid treatment. For example, with regard to activity of FOXO1, activity of Atrogin-1, or activity of MuRF-1, the predetermined level may be 101%, 103%, 105%, 110%, 120%, 130%, or 140% of the activity of FOXO1, activity of Atrogin-1, or activity of MuRF-1 in subjects not having a side effect of a steroid and/or subjects not receiving a steroid treatment.

The method, may further comprise measuring the level of activity of Akt, activity of FOXO1, activity of Atrogin-1, activity of MuRF-1, or a combination in a subject. The subject may be a subject having a side effect of a steroid, e.g., glucocorticoid and/or a subject not having a side effect of a steroid and/or a subject not receiving a steroid treatment. The measuring may be conducted for a cell, for example a cell from a region (e.g., tissue) of a patient having a side effect of a steroid or corresponding region in a subject not having a side effect of a steroid. The cell may include a muscle cell, skin cell, liver cell, gastrointestinal cell, cartilage cell, bone cell, kidney cell, or immune cell. The immune cell includes white blood cell such as B cell, and T cell. The measuring may be conducted by a known method in the art, for example, ELISA, immunohistochemistry, western blotting etc. Measuring the level of activity of Akt, and activity of FOXO1 may include measuring the level of activated Akt or activated FOXO1, for example, phosphorylated FOXO1-p (Ser256), and the phosphorylated Akt-p (Ser473). The measuring the level of activated Akt or activated FOXO1 may include measuring the activated Akt or activated FOXO1 by using a binding material such as an antibody specifically binding to the activated Akt or activated FOXO1, for phosphorylated FOXO1-p (Ser256), and the phosphorylated Akt-p (Ser473). Measuring the level of activity of Atrogin-1, and activity of MuRF-1 may include measuring the expression level of Atrogin-1 gene, and MuRF-1 gene, for example, in transcription level or a translation level. Method of measuring the transcription level is known in the art, for example, including southern blot, nucleic acid amplification method such PCR, RT-PCR, etc. Methods of measuring the translation level are known in the art, for example, including western blot, ELISA, immunohistochemistry etc.

The method may also include identifying or selecting a subject suitable for treatment or prevention of a side effect of a steroid. The identification can be performed, e.g., by measuring the level of Akt activity, activity of FOXO1, activity of Atrogin-1, activity of MuRF-1, or a combination in a subject or biological sample from a subject, wherein a patient is selected if Akt activity is decreased, FOXO1 activity is increased, Atrogin-1 activity is increased, or MuRF-1 activity is increased as compared to the activity levels of the same proteins in a subject not undergoing steroid therapy. Determining whether activity levels are increased or decreased relative to a subject not undergoing steroid therapy can be performed by comparing the activity levels of the patient or biological sample from the patient to a control, as described herein.

The subject may include a mammal, for example, a human, a cow, a horse, a pig, a dog, a sheep, a goat, or a cat. The human may be male or female.

Upon the administration of the dapsone composition, an increase in activity of Akt, a decrease in activity of FOXO1, a decrease in activity of Atrogin-1, a decrease in activity of MuRF-1, a decrease in phosphorylation of a glucocorticoid receptor, a decrease in nuclear translocation of the phosphorylated glucocorticoid receptor, or a combination thereof may be achieved.

The administration of the composition may be performed before, simultaneously, or after administering a steroid drug.

The steroid may include glucocorticoid. The steroid may be, for example, at least one selected from the group consisting of hydrocortin, cortisone, prednisolone, methyl prednisolone, triamcinolone, triamcinolone acetonide, parametrasone, dexamethasone, betamethasone, hexoestrol, methimazole, fluocinonide, fluocinolone acetonide, fluorometholone, beclometasone dipropionate, estriol, diflorasone diacetate, diflucortolone valerate, and difluprednate.

The dapsone, the pharmaceutically acceptable salt, the solvate, the polymorph, of a combination thereof may be administered in a range of about 0.1 mg to about 1,000 mg, e.g., about 0.1 mg to about 500 mg, 0.1 mg to about 100 mg, 0.1 mg to about 50 mg, 0.1 mg to about 25 mg, 1 mg to about 1,000 mg, 1 mg to about 500 mg, 1 mg to about 100 mg, 1 mg to about 50 mg, 1 mg to about 25 mg, 5 mg to about 1,000 mg, 5 mg to about 500 mg, 5 mg to about 100 mg, 5 mg to about 50 mg, 5 mg to about 25 mg, 10 mg to about 1,000 mg, 10 mg to about 500 mg, 10 mg to about 100 mg, 10 mg to about 50 mg, or about 10 mg to about 25 mg, per kilogram (kg) of a subject's body weight.

According to another embodiment, there is provided a method of achieving an increase in activity of Akt, a decrease in activity of FOXO1, a decrease in activity of Atrogin-1, a decrease in activity of MuRF-1, a decrease in phosphorylation of a glucocorticoid receptor, a decrease in nuclear translocation of the phosphorylated glucocorticoid receptor, or a combination thereof.

The term "dapsone, a pharmaceutically acceptable salt, a solvate, a polymorph, or a combination thereof" may be the same as defined in connection with the descriptions above.

Hereinafter, one or more embodiments of the present invention will be described in detail with reference to the following examples. However, these examples are not intended to limit the scope of the one or more embodiments of the present invention.

Example 1

Confirmation of Effects of Dapsone on Inhibiting Side Effects of Glucocorticoid The effects of dapsone on intracellular signal transduction affected by glucocorticoid were confirmed, and accordingly, the effects of dapsone on inhibiting a side effect of glucocorticoid were also confirmed. Glucocorticoid used herein was dexamethasone.

(1) Confirmation of Degree of Expression of Phosphorylated Glucocorticoid Receptor First, a C2C12 cell line (mouse gastrocnemius muscle, ATCC® (CRL-1772™)) was inoculated in a 10% FBS/DMEM culture medium in a 60 mm culture dish. When the cells were grown to about 70% confluency in a 5% $CO_2$ incubator at a temperature of 37° C., the culture medium was changed to a 2% FBS/DMEM culture medium to allow complete differentiation after incubation for 4 days. The C2C12 cell line is a mouse myoblast cell line obtained through continuous culture of myoblasts that are cultured from the gastrocnemius muscle of C3H mice. When the cells were completely differentiated, the medium was removed and changed to 4 mL of a fresh medium containing 20 µM of dapsone to allow incubation for 12 hours. Here, 1 µM of dexamethasone was added thereto and cultured together for 2 hours and 6 hours as described above.

After the medium was removed from the culture and the cells were collected therefrom, 500 µl of an RIPA lysis buffer (including 20 mM Tris-HCl (pH 7.5), 150 mM NaCl, 1 mM $Na_2EDTA$, 1 mM EGTA, 1% NP-40, 1% sodium deoxycholate, 2.5 mM sodium pyrophosphate, 1 mM beta-glycerophosphate, 1 mM $Na_3VO_4$, and 1 µg/ml leupeptin) was added for lysing the cells. Then, the resulting lysates were subjected to electrophoresis and western blot analysis with respect to phosphorylated glucocorticoid receptors. A primary antibody used in the western blot analysis was an HRP-conjugated rabbit anti-GR-P antibody (Jackson ImmunoResearch) that is specific to the phosphorylated glucocorticoid receptors.

In addition, a confocal fluorescence microscope (LSM 710, Carl Zeiss Micro Imaging GmbH, Germany) was used to confirm the degree of nuclear translocation of the phosphorylated glucocorticoid receptors GR-p. In addition, the medium was removed from the differentiated C2C12 muscle cell culture and changed to fresh media, each of which includes 0 µM or dapsone and 20 µM of dapsone, to allow pre-treatment for 12 hours. Here, 1 µM of dexamethasone was added thereto and cultured for 2 hours, and then, the cells were fixed with 4% formaldehyde at room temperature for 30 minutes. The cells were subjected to a blocking process in PBS containing 3% bovine serum albumin (BSA) at room temperature for 1 hour. Next, a secondary antibody, i.e., an anti-rabbit IgG antibody conjugated to green-fluorescent Alexa Fluor 488®, which was diluted in the BSA-containing PBS at a ratio of 1:2000, was incubated in the media at room temperature for 1 hour. The media were each transferred to a glass slide to which a single drop of 50% glycerol was instilled. The LSM 710 fluorescence microscope (Carl Zeiss Micro Imaging GmbH, Germany) was used to observe green fluorescence of the GR-p, so as to confirm the nuclear translocation of the GR-p.

In addition, the medium was removed from the differentiated C2C12 muscle cell culture and changed to fresh media, each of which includes 0 µM or dapsone and 20 µM of dapsone, to allow incubation for 12 hours. Here, 1 µM of dexamethasone was added thereto and cultured for 2 hours, and then, the culture medium was replaced by a cold PBS buffer. The cells were collected by performing centrifugation at 2,000 rpm for 5 minutes. The cells were incubated in 200 µL of a hypotonic buffer (including 10 mM Tris-HCl (pH6.7), 0.2 mM of $MgCl_2$, 1 mM of EGTA, 0.05 mM of leupeptin, 1 mM of PMSF, and 1 µM of pepstatin A) for 5 minutes for lysing the cells. Each sample of the media was subjected to refrigerated centrifugation at 1,500 rpm for 10 minutes to separate and collect supernatant (resulting in cytosol fraction). The pellets, except the supernatant, were washed twice with cold PBS and left in 100 µL of a lysis buffer (including 20 mM of Tris-HCl (pH 6.7), 70 mM of NaCl, 10% glycerol, 1% Triton X-100, 0.5% Nonidet P-40, 300 U/ml DNAseI (Sigma), 0.05 mM of leupeptin, 1 mM of PMSF, and 1 µM of pepstatin A) for 30 minutes, and accordingly, a supernatant was obtained therefrom by performing centrifugation at 1,200 rpm for 5 minutes (resulting in nuclear fraction). Then, electrophoresis and western blot analysis were performed on the separated and obtained cytosol and nuclear fractions. These cytosol and nuclear fractions were used to confirm normal fraction separation by using an anti-COX1 antibody (Cell Signaling Technology, USA) and an anti-lamin antibody (Cell Signaling Technology, USA), respectively.

FIG. 1 is a photograph showing results of western blot analysis with respect to the phosphorylated glucocorticoid receptor in the case of culturing C2C12 myoblasts in the presence of dexamethasone and/or dapsone. In FIG. 1, 'DEX' indicates dexamethasone, 'GR-p' indicates the phosphorylated glucocorticoid receptor, 'Control' indicates a control group treated with neither dexamethasone nor dapsone, and 'DDS' indicates dapsone. As shown in FIG. 1, the amount of the phosphorylated glucocorticoid receptor GR-p was increased in the presence of dexamethasone DEX, but was decreased in the presence of both dexamethasone DEX and dapsone DDS as compared to DEX only.

Figure 2:
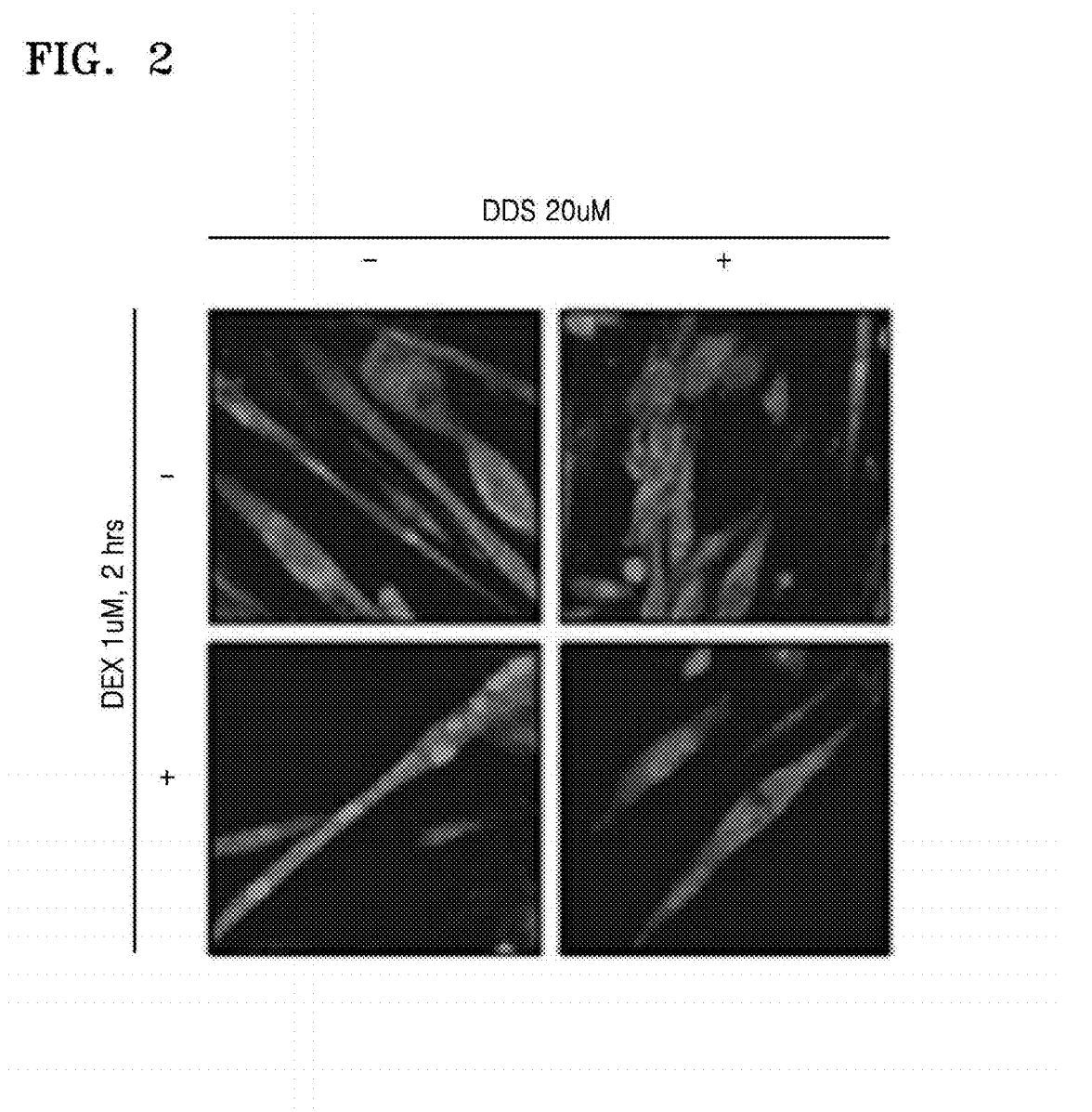
FIG. 2 is a diagram of the degree of nuclear translocation of GR-p confirmed by using a confocal fluorescent microscope (LSM 710, Carl Zeiss Micro Imaging GmbH, Germany) of C2C12 myoblasts cultured for 2 hours in the presence of 1 µM of dexamethasone and/or 20 µM of dapsone.

FIG. 2 is a diagram showing results of the degree of nuclear translocation of the phosphorylated glucocorticoid receptor GR-p that is confirmed by using a confocal fluorescent microscope after culturing C2C12 myoblasts for 2 hours in the presence of 1 µM of dexamethasone and/or 20 µM of dapsone. In FIG. 2, 'DEX' and 'DDS' indicate the same substances as in FIG. 1. As shown in FIG. 2, the degree of the nuclear translocation of the phosphorylated glucocorticoid GR-p was decreased in the presence of dapsone DDS as compared to DEX-only treatment. That is, through comparison of the top left image with the top right image, and the bottom left image with the bottom right image, it was confirmed that the amount of fluorescence was decreased in the nucleus of the cells, as shown in both right images.

Figure 3:
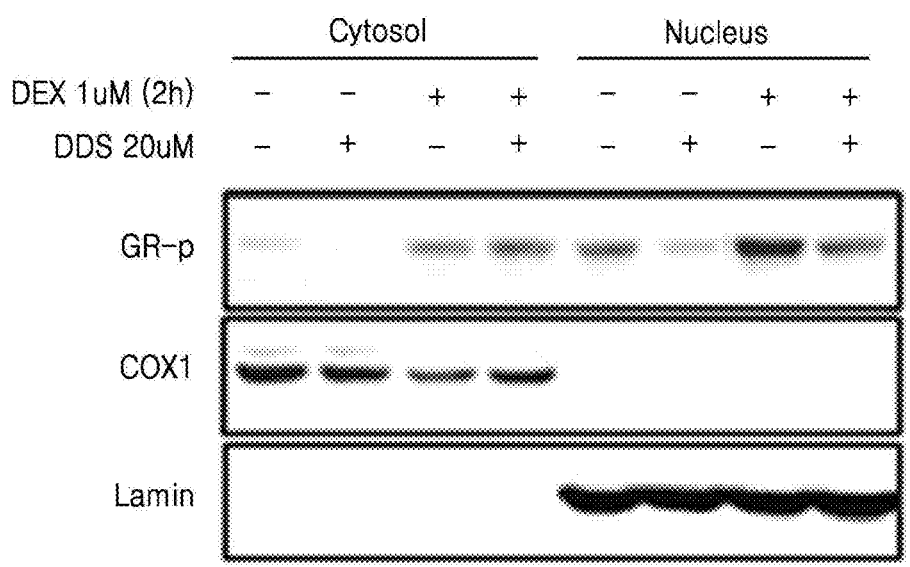
FIG. 3 is a western blot analysis of cytosolic and nuclear fractions of specified cell proteins in cells incubated with 1 µM of dexamethasone and/or 20 µM of dapsone.

FIG. 3 is a photograph showing results of western blot analysis in regard to the cytosol and nuclear fractions. In FIG. 3, 'DEX', 'DDS', and 'GR-p' indicate the same substances as in FIG. 1, and 'COX1' indicates cyclooxygenase I, which is a cytosol marker of each substance, and 'Lamin' indicates a marker of the nuclear fraction of each substance. As shown in FIG. 3, it was confirmed that the amount of the phosphorylated glucocorticoid receptor GR-p in the nucleus was significantly decreased in the presence of both dexamethasone DEX and dapsone DDS, as compared with that in the presence of only dexamethasone. That is, the presence of dapsone decreased the nucleus translocation of the phosphorylated glucocorticoid receptor GR-p, and accordingly it was confirmed that dapsone had functions of blocking or inhibiting the signaling of the phosphorylated glucocorticoid receptor GR-p. As a result, it is now known that dapsone is capable of decreasing or removing a side effect caused by dexamethasone DEX.

(2) Confirmation of Factors of Atrophy

Next, the activity of factors of atrophy caused by dexamethasone was confirmed.

A C2C12 cell line (mouse gastrocnemius muscle, ATCC®CRL-1772™) was inoculated in a 10% FBS/DMEM culture medium in a 60 mm culture dish. When the cells were grown to about 70% confluency in a 5% $CO_2$ incubator at a temperature of 37° C., the culture medium was changed to a 2% FBS/DMEM culture medium to allow complete differentiation after incubation for 4 days. The C2C12 cell line is a mouse myoblast cell line obtained through continuous culture of myoblasts that are cultured from the gastrocnemius muscle of C3H mice. When the cells were completely differentiated, the medium was removed and changed to 4 mL of fresh media, each of which contained 0 µM of dapsone, 0.1 µM of dapsone, 1 µM of dapsone, and 20 µM of dapsone, to allow incubation for 12 hours. Here, 1 µM of dexamethasone was added thereto and cultured together for 2 hours as described above.

After the medium was removed from the culture and the cells were collected therefrom, 500 µl of an RIPA lysis buffer (including 20 mM Tris-HCl (pH 7.5), 150 mM NaCl, 1 mM $Na_2EDTA$, 1 mM EGTA, 1% NP-40, 1% sodium deoxycholate, 2.5 mM sodium pyrophosphate, 1 mM beta-glycerophosphate, 1 mM $Na_3VO_4$, and 1 µg/ml leupeptin) was added for lysing the cells. Then, the resulting lysates were subjected to electrophoresis and western blot analysis using a rabbit antibody as a primary antibody and an HRP-conjugated anti-rabbit antibody as a second antibody (Jackson ImmunoResearch) that are specific to the phosphorylated glucocorticoid receptors (glucocorticoid receptor-S211-p: GR-p), the phosphorylated FOXO1-p (Ser256, Cell Signaling Technology, USA), and the phosphorylated Akt-p (Ser473, Cell Signaling Technology, USA). Here, Tubulin (Cell Signaling Technology, USA) was used as a loading control for the analysis.

Figure 4:
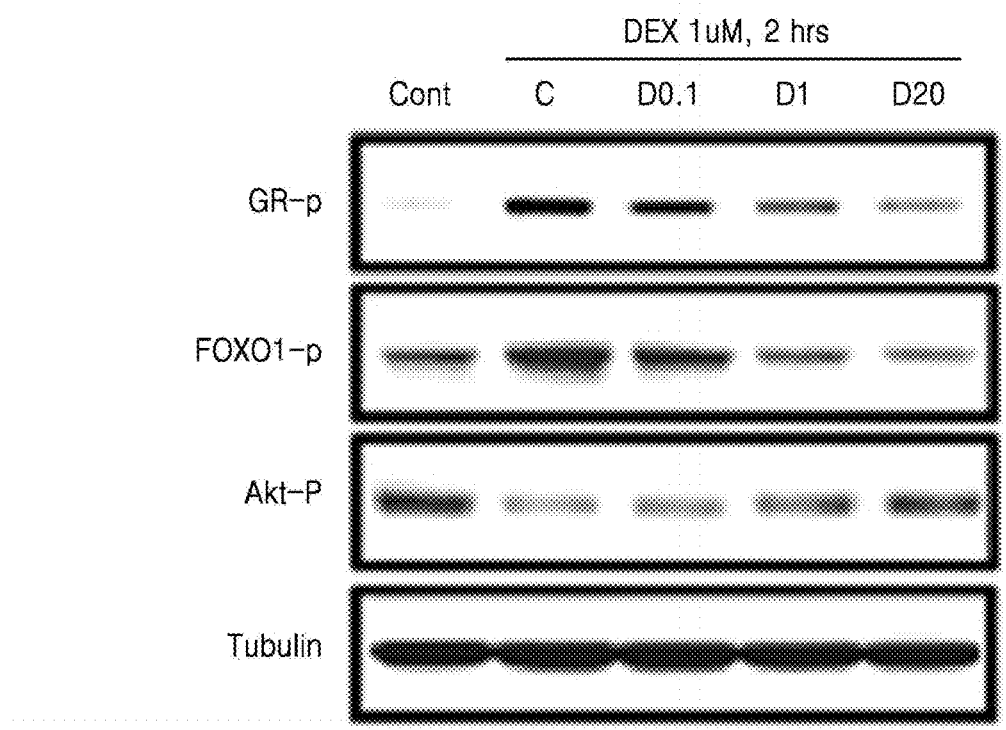
FIG. 4 is a western blot analysis of GR-p, phosphorylated FOXO1 (FOXO1-p), and phosphorylated Akt (Akt-p) in C2C12 myoblasts cultured in the presence of dexamethasone and/or dapsone.

FIG. 4 is a photograph showing results of western blot analysis with respect to the phosphorylated glucocorticoid receptor GR-p, the phosphorylated FOXO1-p, and the phosphorylated Akt-p in the case of culturing C2C12 myoblasts in the presence of dexamethasone and/or dapsone. In FIG. 4, 'Cont' indicates a control group treated with neither dexamethasone nor dapsone, 'C' indicates a group that is not treated with dapsone, and 'D0.1', 'D1', and 'D20' each indicate a group treated with 0.1 µM of dapsone, 1.0 µM of dapsone, and 20 µM of dapsone. As shown in FIG. 4, the amounts of the GR-p and the FOXO1-p were increased in the presence of dexamethasone, but in a concentration-dependent manner, the amount of the GR-p was decreased in the presence of both dexamethasone and dapsone. The amount of the Akt-p was decreased in the presence of dexamethasone, but in a concentration-dependent manner, the amount of the Akt-p was increased in the presence of both dexamethasone and dapsone. As a result, it was confirmed that dexamethasone was characterized by protein degradation that may cause atrophy, and that is, dexamethasone increased the amounts of the GR-p protein and the FOXO1-p protein while the amount of the Akt-p protein, which is important for the synthesis of the protein, decreased. However, in the presence of both dexamethasone and dapsone, the amounts of the GR-p protein and the FOXO1-p protein were decreased while the amount of the Akt-p protein was increased.

(3) Confirmation of Factors of Breakdown of Muscle Protein

Next, the activity of factors of breakdown of muscle proteins caused by dexamethasone and/or dapsone was confirmed.

A C2C12 cell line (mouse gastrocnemius muscle, ATCC®CRL-1772™) was inoculated in a 10% FBS/DMEM culture medium in a 60 mm culture dish. When the cells were grown to about 70% confluency in a 5% $CO_2$ incubator at a temperature of 37° C., the culture medium was changed to a 2% FBS/DMEM culture medium to allow complete differentiation after incubation for 4 days. The C2C12 cell line is a mouse myoblast cell line obtained through continuous culture of myoblasts that are cultured from the gastrocnemius muscle of C3H mice. When the cells were completely differentiated, the medium was removed and changed to 4 mL of fresh media, each of which contained 0.0 µM of dapsone, 0.1 µM of dapsone, 1 µM of dapsone, and 20 µM of dapsone, to allow incubation for 12 hours. Here, 1 µM of dexamethasone was added thereto and cultured together for 24 hours as described above.

After the medium was removed from the culture and the cells were collected therefrom, 500 µl of an RIPA lysis buffer was added for lysing the cells. Then, the resulting lysates were subjected to electrophoresis and western blot analysis with respect to Atrogin-1, MuRF-1, and α-tubulin. A primary antibody used in the western blot analysis was a rabbit anti-Atrogin-1 antibody (ECM Bioscience), a MuRF-1 antibody (GeneTax), and α-tubulin (Cell Signaling Technology, USA) antibody, and a secondary antibody used in the western blot analysis was an HRP-conjugated anti-rabbit antibody (Jackson ImmunoResearch).

In addition, the culture medium of the differentiated C2C12 muscle cells was removed and changed to fresh media, each of which contained 0 µM of dapsone and 20 µM of dapsone, to allow incubation for 12 hours. Here, 1 µM of dexamethasone was added thereto and incubated for 24 hours. Then, the amounts of the expressed mRNA of the Atrogin-1 and MuRF-1 among the C2C12 cells were confirmed. Here, the complete RNA was separated by using a Trizol reagent (Invitrogen). The analysis of the mRNAs of Atrogin-1 and MuRF-1 was performed by using a real time PCR (MyiQPCR instrument, BioRad), which is a device for measuring reverse transcription and SYBR Green. The resulting amounts then normalize to the amount of GAPDH mRNA. The amplification of Atrogin-1, MuRF-1, and GAPDH mRNAs was performed by using an oligonucleotide primer set of SEQ ID NOS: 1 and 2, an oligonucleotide primer set of SEQ ID NOS: 3 and 4, and an oligonucleotide primer set of SEQ ID NOS: 5 and 6.

Figure 5A:
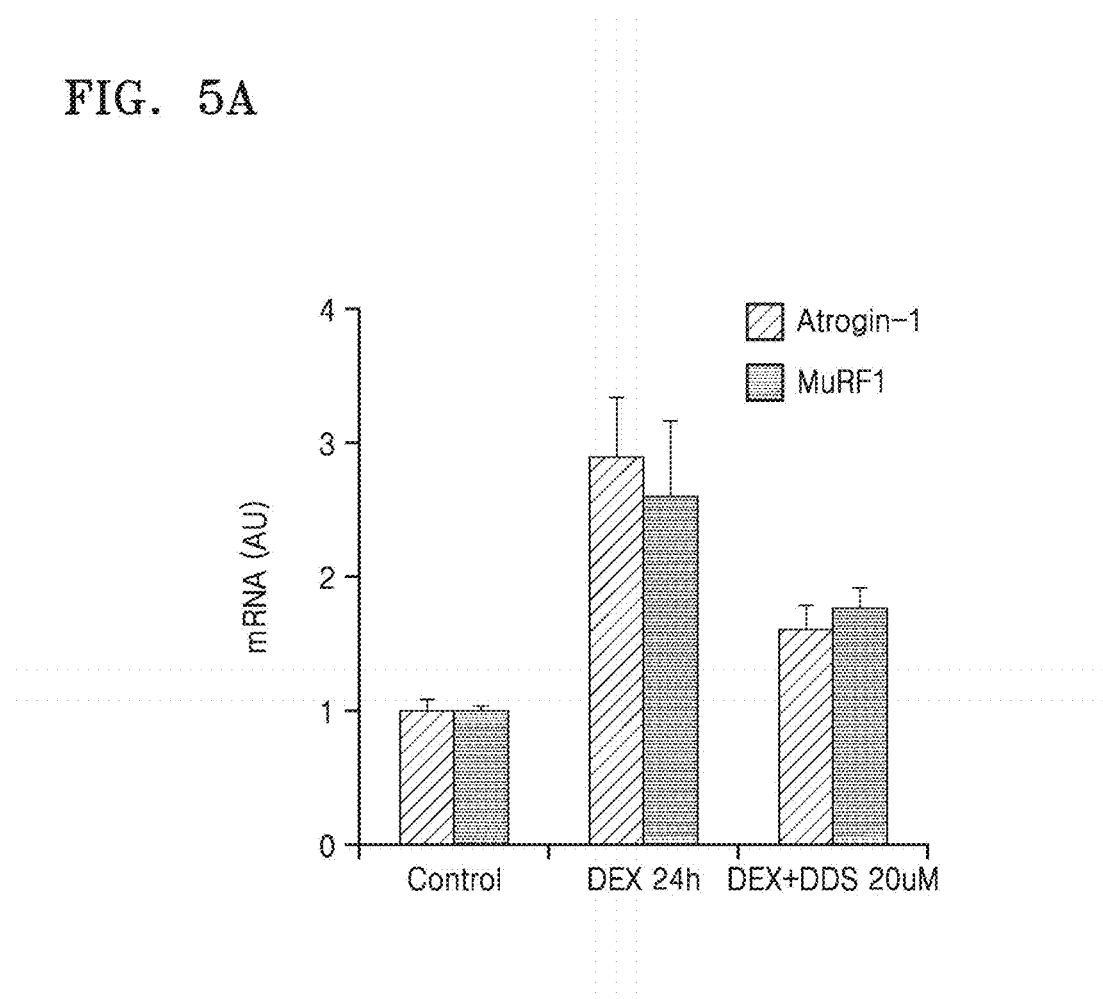
FIG. 5A is a graph Atrogin-1 and MURF-1 mRNA expression levels as measured by PCR (AU=arbitrary units) in C2C12 myoblasts cultured in the presence of dexamethasone and/or dapsone.
Figure 5B:
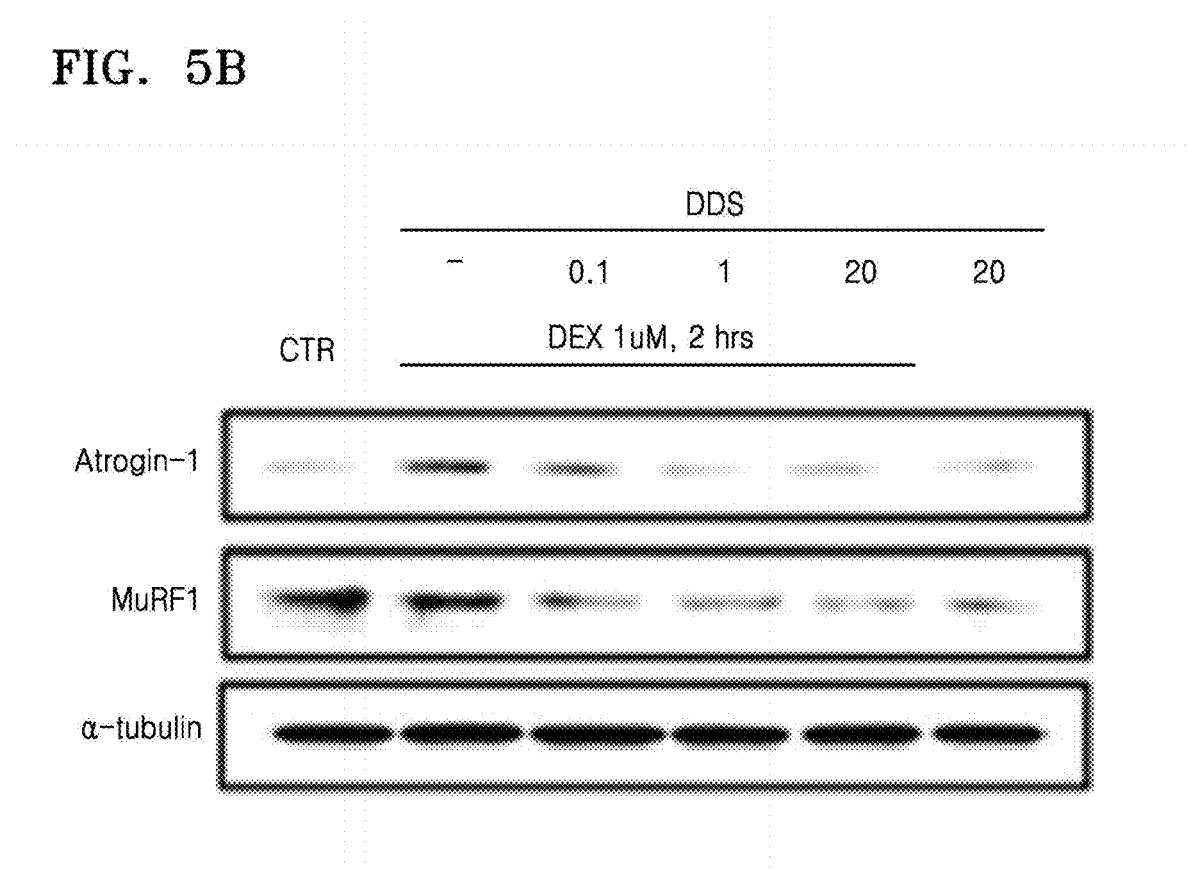
FIG. 5B is a western blot analysis showing Atrogin-1 and MURF-1 protein expression levels in C2C12 myoblasts cultured in the presence of dexamethasone and/or dapsone.

FIGS. 5A and 5B are photographs showing Atrogin-1 and MURF-1 with mRNA and protein expression levels thereof in the case of culturing C2C12 myoblasts in the presence of dexamethasone and/or dapsone. FIG. 5A shows the results of the mRNA levels of Atrogin-1 and MURF-1 that were measured by a real time-PCR after incubation for 24 hours in the presence of 1 µM of dexamethasone or in the presence of 1 µM of dexamethasone and 20 µM of dapsone. Here, 'Control' indicates a control group that was treated with neither 20 µM of dapsone nor 1 µM of dexamethasone. As shown in FIG. 5A, the mRNA levels of Atrogin-1 and MURF-1 were significantly decreased in the presence of both dexamethasone and dapsone. FIG. 5B shows the results of the protein levels measured by western blot analysis after incubation for 2 hours in the presence of 1 µM of dexamethasone, in the presence of 1 µM of dexamethasone and dapsone at a specific concentration (e.g., 0.1 µM, 1 µM, or 20 µM), or in the presence 20 µM of dapsone. Here, 'CTR' indicates a control group treated with neither 20 µM of dapsone nor dexamethasone. As shown in FIG. 5B, the proteins levels of Atrogin-I and MURF-1 were significantly decreased in the presence of both dexamethasone and dapsone, in a concentration-dependent manner.

Therefore, in the presence of dapsone, the amounts of proteases, i.e., Atrogin-1 and MURF-1, that break down muscle proteins were decreased, and accordingly, dapsone may be capable of preventing or treating muscle loss.

(4) Confirmation of Effects of Dapsone on Muscle Contractility and Muscle Fatigability The SOL muscle was separated from a female mouse (which weighs about 20 g) aged about 3 months. The mouse was anesthetized by sodium pentobarbital injection (100 mg/kg body weight). The SOL muscle, which is a type I muscle, was separated by paying attention to each hind-limb of the mouse while maintaining ligaments from both hind-limbs without damaging the SOL muscle. Then, the separated SOL muscle was put in an oxygen-treated Ringer's solution (118 mM NaCl, 4.75 mM KCl, 2.5 mM $CaCl_2$, 1.18 mM $MgSO_4$, 1.18 mM $NaH_2PO_4$, 24.8 mM $NaHCO_3$, 10 mM glucose, and 0.02 g/l tubocurarine chloride, 25° C., pH 7.4) (Sigma Aldrich), set, and stabilized. One side of the separated SOL muscle was filled with the Ringer's solution to fix the separated SOL muscle on a tissue bath with smooth oxygen supply while the other side of the separated SOL muscle was fixed on a FT03 isometric force transducer (Grass Instruments, West Warwick, USA). Here, the muscle twitching was adjusted according to the intensity of the electric field stimulation. In order to maximize the muscle functions, the length of the muscle was measured at a point where the muscle showed a maximum response through twitch stimulation at a frequency of 0.2 Hz (100 V), and the length was referred to as 'Lo'. Here, the muscle contractility value (mN) represents the muscle twitch contraction.

Figure 6:
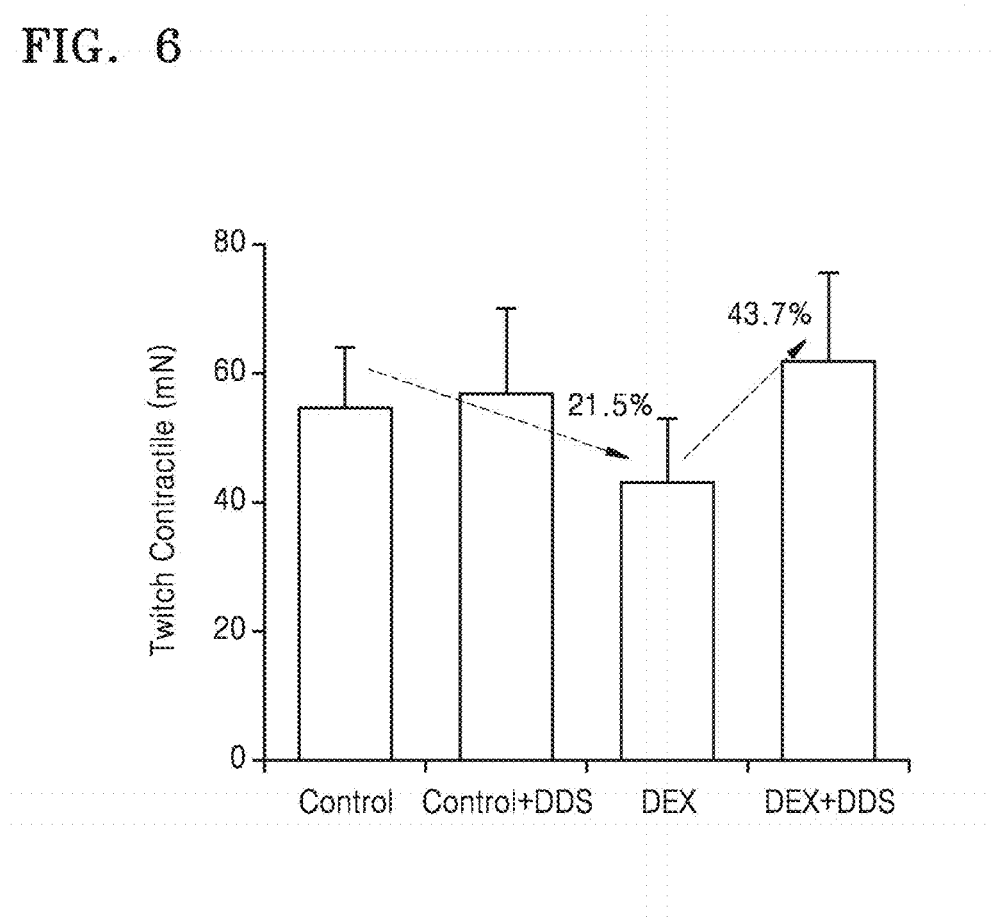
FIG. 6 is a graph of muscle contractility (twitch contractile (mN)) at a frequency of 0.2 Hz (100 V) in the SOL muscle of the hind limb of mice under different treatment conditions.

FIG. 6 shows the results of measuring the muscle contractility at a frequency of 0.2 Hz (100 V). In FIG. 6, 'Control' indicates a negative control group using the SOL muscle of the hind-limb of a mouse that was not fed on dapsone, 'Control+DDS' indicates a group using the SOL muscle of the hind-limb of a mouse that was fed on 2 mg/kg of dapsone for 3 weeks, 'DEX' indicates a group using the SOL muscle of the hind-limb of a mouse that was fed on 4 mg/kg of dexamethasone for 3 weeks, and 'DEX+DDS' indicates a group using the SOL muscle of the hind-limb a mouse that was on 4 mg/kg of dexamethasone and 2 mg/kg of dapsone for 3 weeks. In FIG. 6, the vertical line of the group shows twitch contractility. As shown in FIG. 6, the twitch contractility of the muscle of the mouse that was fed on dexamethasone was decreased by 21.5%, as compared with that of the muscle of the mouse in the control group. However, the twitch contractility of the muscle of the mouse that was fed on both dexamethasone and 2 mg/kg of dapsone was increased by 43.7%, as compared with that of the muscle of the mouse that has been fed on dexamethasone. That is, it is now known that dapsone has effects on increasing muscle contractility.

In addition, according to the muscle contraction stimulation system that takes into account measurement conditions in FIG. 6, the SOL muscles formed the highest plateau under conditions of a frequency of 150 Hz and a voltage of 100 V for 800 ms, showing tendency of being stabilized in the graph showing the muscle contraction. This highest plateau value is referred to as peak isometric force for each muscle, and a unit used herein is mM. In order to induce muscle fatigability, the stimulations were continuously applied to the muscle every 2 seconds for 30 seconds. The initial stimulation was set to be 100%, and the decrease in the muscle contractility upon every stimulation was shown as ratios.

Figure 7:
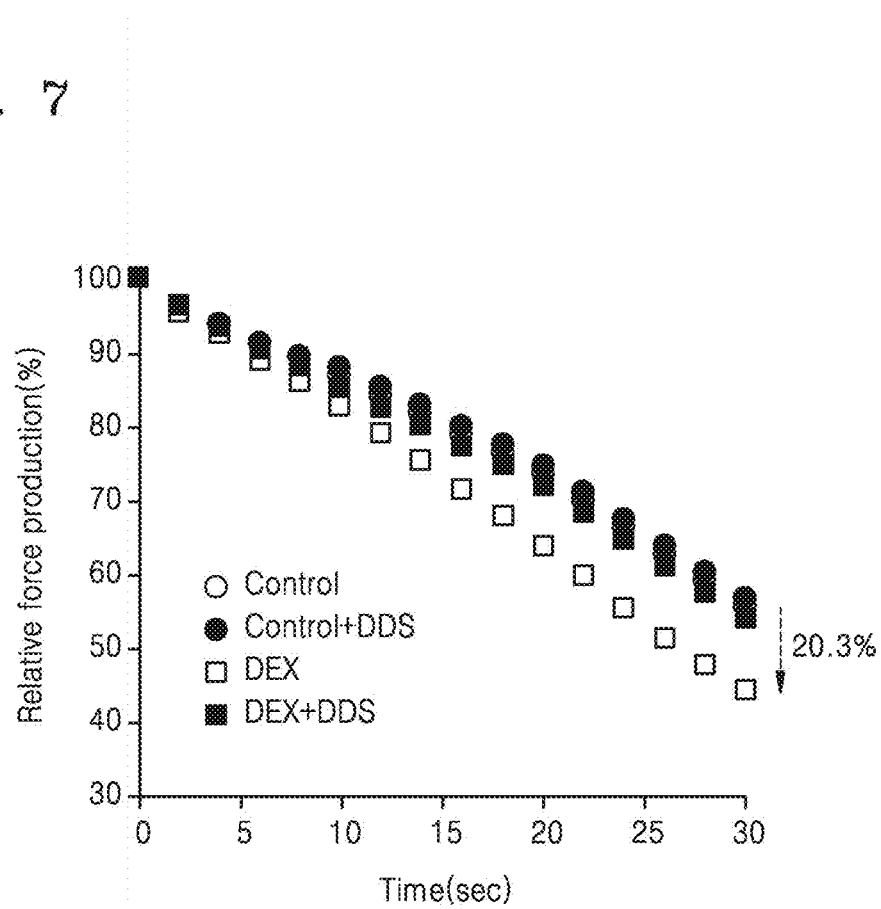
FIG. 7 is a graph of relative force production plotted against time for mice of specified treatment groups illustrating the effects of dapsone on muscle fatigability.

FIG. 7 shows the results of effects of dapsone on muscle fatigability. As shown in FIG. 7, the degree of the muscle fatigability was increased upon intake of dexamethasone. However, the muscle fatigability was decreased upon intake of both dexamethasone and dapsone by 20.3%, as compared with the muscle fatigability upon intake of only dexamethasone. In FIG. 7, the horizontal axis of the graph indicates time (in seconds) and the vertical axis of the graph indicates relative force production.

As described above, according to the one or more of the above exemplary embodiments, a composition for preventing or treating a side effect of a steroid in a subject may be used to prevent or treat a side effect of a steroid in a subject.

According to the one or more of the above exemplary embodiments, a composition for increasing activity of Akt, decreasing activity of FOXO1 compared to a control subject, decreasing activity of Atrogin-1 compared to a control subject, decreasing activity of MuRF-1 compared to a control subject, decreasing phosphorylation of a glucocorticoid receptor compared to a control subject, decreasing nuclear translocation of the phosphorylated glucocorticoid receptor compared to a control subject, or a combination thereof may be used to increase activity of Akt, decrease activity of FOXO1 compared to a control subject, decrease activity of Atrogin-1, decrease activity of MuRF-1 compared to a control subject, decrease phosphorylation of a glucocorticoid receptor compared to a control subject, decrease nuclear translocation of the phosphorylated glucocorticoid receptor compared to a control subject, or perform a combination thereof.

According to the one or more of the above exemplary embodiments, a method of preventing or treating a side effect of a steroid may be used to prevent or treat a side effect of a steroid in an efficient manner.

According to the one or more of the above exemplary embodiments, a method of further achieving an increase in activity of Akt compared to a control subject, a decrease in activity of FOXO1 compared to a control subject, a decrease in activity of Atrogin-1 compared to a control subject, a decrease in activity of MuRF-1 compared to a control subject, a decrease in phosphorylation of a glucocorticoid receptor compared to a control subject, a decrease in nuclear translocation of the phosphorylated glucocorticoid receptor compared to a control subject, or a combination thereof may be used to increase activity of Akt compared to a control subject, decrease activity of FOXO1 compared to a control subject, decrease activity of Atrogin-1 compared to a control subject, decrease activity of MuRF-1 compared to a control subject, decrease phosphorylation of a glucocorticoid receptor compared to a control subject, decrease nuclear translocation of the phosphorylated glucocorticoid receptor compared to a control subject, or perform a combination thereof in an efficient manner.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a side effect of a glucocorticoid in a subject, the method comprising:
   selecting a subject for administration of dapsone to reduce the side effect of a glucocorticoid treatment, wherein selecting the subject comprises measuring the level of Akt activity, FOXO1 activity, Atrogin-1 activity, MuRF-1 activity, or a combination thereof in a subject or biological sample from a subject, and selecting the subject for dapsone administration if Akt activity is decreased, FOXO1 activity is increased, Atrogin-1 activity is increased, or MuRF-1 activity is increased as compared to the activity levels of the same proteins in a subject not undergoing steroid treatment; and
   administering dapsone, a pharmaceutically acceptable salt, a solvate, or a combination thereof to the subject treated with a glucocorticoid and exhibiting a side effect of a glucocorticoid, wherein the dapsone, a pharmaceutically acceptable salt, a solvate, or a combination thereof treats the side effect.

2. The method of claim 1, wherein the side effect of the glucocorticoid is caused by a treatment using the glucocorticoid, by an increase in the amounts of the glucocorticoid administered to the subject compared to a control subject, or a combination thereof.

3. The method of claim 2, wherein the side effect of the glucocorticoid is at least one selected from the group consisting of amyotrophy, hypofunction in muscular strength, myalgia, arthralgia, impaired glucose tolerance, low appetite, weight loss, bone hypometabolism, low immunity, and fatigability.

4. The method of claim 1, wherein the side effect of glucocorticoid is caused by inhibited activity of Akt, increased activity of FOXO1, increased activity of Atrogin-1, increased activity of MuRF-1, or a combination thereof, in the subject treated with a glucocorticoid as compared to the activity levels of Akt, FOXO1, Atrogin-1, or MuRF-1 of a patient not undergoing steroid therapy.

5. The method of claim 1, wherein the administering of the dapsone, a pharmaceutically acceptable salt, a solvate, or a combination thereof treats a side effect of a glucocorticoid in a subject by increasing the activity of Akt, decreasing the activity of FOXO1, decreasing the activity of Atrogin-1, decreasing the activity of MuRF-1, decreasing the phosphorylation of a glucocorticoid receptor, decreasing the nuclear translocation of a phosphorylated glucocorticoid receptor, or a combination thereof, in the subject treated with a glucocorticoid.

6. The method of claim 1, wherein the administering of the dapsone, a pharmaceutically acceptable salt, a solvate, or a combination thereof is performed before, simultaneously, or after the administration of a glucocorticoid drug.

7. The method of claim 1, wherein the glucocorticoid is at least one selected from cortisol, hydrocortin, cortisone, prednisolone, methyl prednisolone, triamcinolone, triamcinolone acetonide, paramethasone, dexamethasone, betamethasone, hexoestrol, methimazole, fluocinonide, fluocinolone acetonide, fluorometholone, beclometasone dipropionate, estriol, diflorasone diacetate, diflucortolone valerate, and difluprednate.

8. The method of claim 1, wherein the dapsone, the pharmaceutically acceptable salt, the solvate, or the combination thereof is administered in dosage of about 0.1 mg to about 1,000 mg per kg of a subject's body weight.

9. The method of claim 1, wherein the side effect is amyotrophy, hypofunction in muscular strength, or a combination thereof.

* * * * *